United States Patent
Ossart

(10) Patent No.: US 9,567,561 B2
(45) Date of Patent: Feb. 14, 2017

(54) SINGLE-USE BIOMASS SENSING DEVICE, METHOD FOR PRODUCING THIS DEVICE AND SINGLE-USE BIOREACTOR INCORPORATING THIS SENSOR

(75) Inventor: Frederic Ossart, Langlade (FR)

(73) Assignee: HAMILTON BONADUZ AG, Bonaduz (CH)

(*) Notice: Subject to any disclaimer, the term of this patent is extended or adjusted under 35 U.S.C. 154(b) by 595 days.

(21) Appl. No.: 13/055,836

(22) PCT Filed: Jul. 24, 2009

(86) PCT No.: PCT/FR2009/051506
§ 371 (c)(1),
(2), (4) Date: Apr. 15, 2011

(87) PCT Pub. No.: WO2010/010313
PCT Pub. Date: Jan. 28, 2010

(65) Prior Publication Data
US 2011/0187388 A1    Aug. 4, 2011

(30) Foreign Application Priority Data

Jul. 25, 2008  (FR) .................................... 08 55138

(51) Int. Cl.
*C12M 1/34* (2006.01)
*G01N 27/22* (2006.01)
(Continued)

(52) U.S. Cl.
CPC ............. *C12M 41/46* (2013.01); *C12M 23/28* (2013.01); *C12M 41/36* (2013.01); *G01N 27/221* (2013.01);
(Continued)

(58) Field of Classification Search
CPC ....... C12M 23/28; C12M 41/36; C12M 41/46; G01N 27/221; G01N 33/48735; Y10T 29/49002
(Continued)

(56) References Cited

U.S. PATENT DOCUMENTS 4,160,205 A    7/1979 Hobbs et al.
2005/0176155 A1  8/2005 Klein et al.
(Continued)

FOREIGN PATENT DOCUMENTS

EP    0036274 A2    9/1981
FR    2812725 A1    2/2002
(Continued)

OTHER PUBLICATIONS

French Search Report dated Mar. 25, 2009 for FA 713819 and FR 0855138.
(Continued)

*Primary Examiner* — Nathan Bowers
*Assistant Examiner* — Lydia Edwards
(74) *Attorney, Agent, or Firm* — Rothwell, Figg, Ernst & Manbeck, P.C.

(57) ABSTRACT

A single-use bioreactor or container including an enclosure provided for containing a biological medium, and at least one device for making at least one impedance measurement in a physical, physico-chemical and/or biological process in this medium. The sensing device is fixed through a wall of the enclosure in such a way as to be an integral part thereof and includes a detection part in direct contact with an inside of the bioreactor or container and a connection part extending towards an outside of the enclosure.

19 Claims, 3 Drawing Sheets

(51) Int. Cl.
*G01N 33/487* (2006.01)
*C12M 1/00* (2006.01)

(52) U.S. Cl.
CPC .... *G01N 33/48735* (2013.01); *Y10T 29/49002* (2015.01)

(58) Field of Classification Search
USPC .......................................... 435/283.1–309.4
See application file for complete search history.

(56) References Cited

U.S. PATENT DOCUMENTS

| | | | |
|---|---|---|---|
| 2005/0272146 | A1 | 12/2005 | Hodge et al. |
| 2007/0157748 | A1 | 7/2007 | Baumfalk et al. |
| 2007/0214872 | A1* | 9/2007 | Ammann et al. ............ 73/53.01 |
| 2009/0139298 | A1* | 6/2009 | Klees et al. .................. 73/1.03 |

FOREIGN PATENT DOCUMENTS

| | | | |
|---|---|---|---|
| FR | 2867278 | A1 | 9/2005 |
| FR | 2867279 | A1 | 9/2005 |
| GB | 1070833 | | 6/1967 |
| GB | 2177801 | A | 1/1987 |
| WO | 91/00903 | A1 | 1/1991 |
| WO | WO 01/79828 | A1 | 10/2001 |
| WO | WO 03/097861 | A1 | 11/2003 |
| WO | 2005/068059 | A1 | 7/2005 |
| WO | WO 2005/085412 | A2 | 9/2005 |
| WO | WO 2005/085818 | A2 | 9/2005 |
| WO | WO 2008155279 | A1 * | 12/2008 |

OTHER PUBLICATIONS

French Search Report dated Feb. 8, 2010 for PCT/FR 2009/051506 filed Jul. 24, 2009.

John P Carvell et al; "New Applications and Methods Utilizing Radio-Frequency Impedance Measurements for Improving Yeast Management"; MBAA Technical Quarterly; vol. 40; No. 1; 2003; pp. 30-38.

John P Carvell et al; "Using capacitance for rapid and reproducible estimation of live yeast cell mass during fermentation"; Australian and New Zealand grapegrower and winemaker; Ryan Publications; Adelaide; AU; No. 466; Jan. 1, 2002; pp. 56-59.

C.L. Davey et al; "Real-time monitoring of the accretion of Rhizopus oligosporus biomass during the solid-substrate tempe fermentation"; World Journal of Microbiology and Biotechnology; Rapid Communications of Oxford; Oxford; GB; vol. 7; No. 2; Mar. 1, 1991; pp. 248-259.

K. Asami et al.; "Dielectric spectroscopy of biological cells"; Bioelectrochemistry and Bioenergetics; vol. 50; No. 2; Aug. 1, 1996; pp. 141-145.

John P Carvell et al.; "The use of capacitance for off-line measurement of viable yeast concentration over a range of sample vialibilities"; Institute of Brewing Asia Pacific Section; Mar. 1998; pp. 22-27.

J.P. Carvell et al.; "Developments in using off-line radio frequency impedance methods for measuring the viable cell concentration in the brewery"; American Society of Brewing Chemists; vol. 58; No. 2; 2000; pp. 57-62.

Carvell J.P.; "A comparison of monitoring yeast fermentations by RF impedance with traditional methods of biomass estimation"; Master Brewers Association of the Americas; Oct. 4-8, 2003; pp. 1-2.

* cited by examiner

SINGLE-USE BIOMASS SENSING DEVICE, METHOD FOR PRODUCING THIS DEVICE AND SINGLE-USE BIOREACTOR INCORPORATING THIS SENSOR

BACKGROUND

The present invention relates to single-use biomass sensing devices. It also relates to a method for producing such sensors, associated with single-use bioreactors or with a probe/support made of stainless steel on standard bioreactors, made of stainless steel and glass.

The development of novel molecules by biotechnological way is still considered as the main direction of pharmaceutical development. Nowadays, the pharmaceutical industry recognizes significant advantages associated with single use:

safety, due to limitation of the risk of cross-contamination,
  and gains in productivity obtained (i) by the reduction of operating costs, in particular labour costs; (ii) by the utilization of a high-density culture which helps to limit culture times and occupation of floor space; and (iii) by a more rapid and less expensive industrial scale application.

Conventionally the bioreactors utilized are reusable, made of a glass or stainless steel tank, requiring their cleaning, sterilization and constant re-validation. These operations, which are increasingly expensive as a result of continuous growth in regulatory and quality requirements, are eliminated by the introduction of single-use solutions.

There is a growing need for equipment such as single-use fermentation bioreactors, "upstream & downstream" storage and preparation tanks. Such systems are necessarily equipped with sensors provided for measuring physico-chemical, biochemical or biophysical parameters. There can in particular be mentioned sensors carrying out impedance spectroscopy, in particular the capacitive technology sensors designed by the present applicant.

These capacitive sensors make it possible to detect relative variations in capacitances of $10^{-5}$ in low-resistance media (a few tens of Ohms). This technique also makes it possible, by means of impedance spectroscopy, to determine the parameters of β dispersion curves (radio frequency). The measurements then provide not only a concentration of living cells but also indications regarding the morphology and the physiological state of the cells. The usual measurement probes are macroscopic in size and intended for stainless steel fermentation tanks. They typically utilize configurations with 4 electrodes in order to be free of the effects of double-layer polarization.

There can in particular be mentioned capacitive sensors specifically dedicated to conductance measurements, in particular for "downstream" type purification applications. These conductance sensors can have the same electrode geometries and structures as capacitive sensors allowing complete measurements of impedance with capacitance and conductance measurements.

The use of an aseptic connector is also known, which makes it possible to introduce solid sensors into a disposable fermenter provided this is in a very protected environment and under a laminar air flow hood. This solution is overall more expensive due to the production and operating cost of the solid sensors: decontamination, removal, cleaning, fitting of the sensor. Moreover, the solid sensors provided in order to equip single-use bioreactors must be sterilized before each use, which does not in itself limit the risk of contamination linked to the sequence of necessary tasks.

SUMMARY

The purpose of the present invention is to remedy these drawbacks by proposing a single-use bioreactor or container incorporating a capacitive sensor which is sufficiently high-performance for applications in a bioreactor, whilst having minimized production and operating costs.

This objective is achieved with a single-use bioreactor or container comprising an enclosure provided for containing a biological medium, and at least one device for making at least one impedance measurement in a physical, physico-chemical and/or biological process in said medium, characterized in that this sensing device is fixed through a wall of said enclosure in such a way as to be an integral part thereof and comprises a detection part in direct contact with the inside of said bioreactor or container and a connection part extending towards the outside of said enclosure.

According to another aspect of the invention, a single-use device is proposed for making at least one impedance measurement in a physical, physico-chemical and/or biological process, comprising means for carrying out at least one impedance measurement in a physical, physico-chemical and/or biological process in said medium, characterized in that it is arranged in order to be fixed through a wall of an enclosure provided for containing a biological medium, in such a way as to be an integral part thereof, and in that it comprises a detection part in direct contact with said biological medium and a connection part extending towards the outside of said enclosure.

In particular, this single-use capacitive device can be specifically dedicated to the measurement of living biomass in a biological medium, using capacitance measurement.

The single-use sensing device according to the invention can be associated in-line with other single-use physical, physico-chemical or biochemical sensors such as sensors of temperature, pH, dissolved oxygen concentration, dissolved $CO_2$ concentration, optical density, pressure, level, ammonium concentration, glycerol concentration, lactate and glucose levels, and more generally any other single-use sensor with a view to improving knowledge and control of a biological culture.

An optical sensor using a single-use fluorescent chip is an advantageous coupling technique and involves the in-line measurement of parameters such as pH, the dissolved oxygen concentration and the dissolved $CO_2$ concentration measurement. It can thus incorporate several single-use sensors on the same support.

Thus with the invention, it becomes possible of produce the first biocompatible and sterilizable in-line single-use multi-sensor system, measuring the key stages of a cell culture, with a view to controlling it according to quantitative and qualifying criteria and objectives of production on any scale. It will also make it possible to couple bio-diagnostics and microtechnologies for the characterization of various biological media.

In a particular embodiment, the sensing device according to the invention is arranged in order to be installed in a sterile envelope for multiple applications.

The sensing device according to the invention can also be arranged in order to be inserted and immersed in an enclosure provided for containing biological cells.

In a variant of the invention, the single-use sensing device according to the invention is arranged in order to be installed in a bioreactor produced preferably for fixed-bed use, i.e. any type of culture of cells on a microcarrier and macro-carrier adherent support or any other application in which the sought measurements result from an adherent-type culture process. It can for example be inserted into a basket immersed in an enclosure provided for containing biological cells the growth model of which is considered static, for example, for the culture of stem cells for medical applications.

In another variant of the invention, the single-use sensing device according to the invention is arranged in order to be installed in a single-use bioreactor.

The fixing means are for example arranged to allow the fixing of the sensor on a side wall or on the base of the single-use bioreactor.

The sensing device according to the invention can also be inserted into a passage made in one wall of the bioreactor and have a detection surface oriented towards and in contact with the inside of this bioreactor.

In an advantageous embodiment, the single-use sensing device comprises electrodes extending over the detection part.

It can be produced in the form of a machined mechanical part arranged for receiving the electrodes on a detection part and measurement signal output means on a connection part.

It can also be produced in the form of an injection-moulded part including the electrodes on a detection part and the measurement signal output means on a connection part.

The measurement signal output means can comprise a connector or a cable or a flexible component.

The electrodes can be produced from metal parts or by deposition of metal on an insulating support which can be a flexible component.

This flexible support can be produced in the form of two insulating films at least one of which supports an electrode produced by deposition and electrically connected to a conductor arranged between the two insulating films.

The single-use sensing device can be arranged in order to be installed in a sterile envelope for multiple uses.

In a particular embodiment variant, the single-use sensing device comprises built-in means for locally processing impedance measurement signals. These built-in means can be provided in order to produce an alarm signal in response to the detection of an anomaly by the built-in processing means.

According to another aspect of the invention, a method is proposed for producing a single-use sensing device according to the invention, implemented in a production environment corresponding to the criteria of asepsis and sterility required for the use of a bioreactor.

In fact, all the techniques implemented (welding, washing, cleaning, bacterial and viral decontamination, mechanical tools, means of analysis) represent a novel production methodology which hitherto had not been implemented for the production of solid and conventional sensors.

The materials utilized for the production of the single-use sensing device are necessarily biocompatible. These materials can advantageously be compatible with gamma-irradiation sterilization before and/or after the installation of the sensing device on the bioreactor.

The present invention is also applicable to off-line measurement methods such as diagnostics for medical use, biological, medical, environmental quality control, or packaging prepared specifically for biological control, and is therefore not limited solely to sterile enclosures with in-line measurement.

In another application of a single-use biomass sensor according to the invention, the latter is mounted on an aseptic enclosure and is optionally associated with a physical or biological sensor in order to produce a disposable biological medium storage container incorporating disposable sensors. The latter make it possible at any time to control the living biomass and other physico-chemical parameters with other associated sensors.

This storage means can be produced from the same sensors and enclosure materials as for the bioreactor application. It makes it possible to detect any biological incident during the storage of the material, without risk of loss of sterility during this control as no sample has been taken.

This application is particularly recommended for the industrial control of biological or chemical material before and after delivery within the framework of quality monitoring of the product. It also provides a certain advantage for any long-term storage for which it is necessary to have regular quality control or to estimate the time limit of a product such as foodstuffs.

It thus becomes possible to produce intelligent packaging making it possible to detect, by means of its incorporated sensors, any anomaly or storage accident and to provide traceability of the transport of compositions, products or foodstuffs involving safety and quality requirements.

BRIEF DESCRIPTION OF THE DRAWINGS

Other advantages and characteristics of the invention will become apparent on examining the detailed description of an embodiment which is in no way limitative, and the attached drawings in which.

DETAILED DESCRIPTION

A description will now be given, with reference to the above-mentioned figures, of several examples of single-use sensors according to the invention, in different configurations of use.

Figure 1:
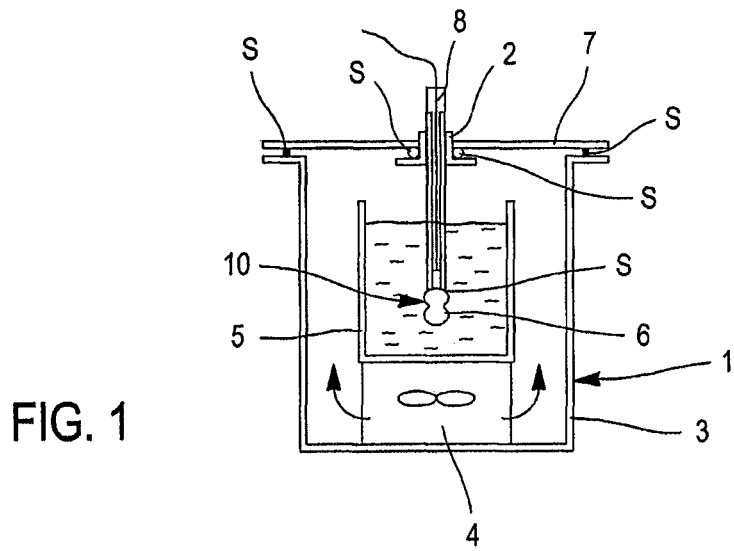
FIG. 1 is a diagrammatic view of a single-use sensor according to the invention utilized in a single-use fixed-bed reactor.

First a description will be given of an example of use of a single-use impedance sensor 10 utilized in a reusable bioreactor 1, with reference to FIG. 1. This bioreactor 1 can, by way of a non-limitative example, be of the type of those marketed by WAVE, SARTORIUS or ATMI.

The impedance sensor utilized can be of the capacitive type such as that marketed by the present applicant and disclosed in the document FR2 812 725. It can also be of the "multisensor" type, such as those comprising optical sensors which are disclosed in the document FR2 867 279 in the name of the present applicant.

The bioreactor 1 comprises, in an enclosure 3, a fixed bed 5 containing biological cells and equipped with a stirrer 4, a lid 7 fixed to the enclosure 3 by welds D and pierced with an opening 2 into which a receiving tube 9 is inserted provided for receiving a single-use impedance sensor 10 equipped with a set of electrodes 6 at its end. These electrodes can be two, four or more in number, depending on the measurement technique implemented. The impedance sensor 10 comprises conductors 8 for delivering the measurement signals generated by this sensor.

Figure 2:
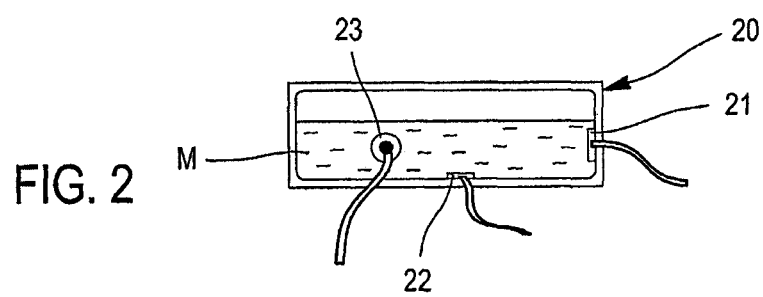
FIG. 2 is a diagrammatic view of a single-use bioreactor for cultures of cells in suspension equipped with single-use sensors according to the invention.
Figure 3:
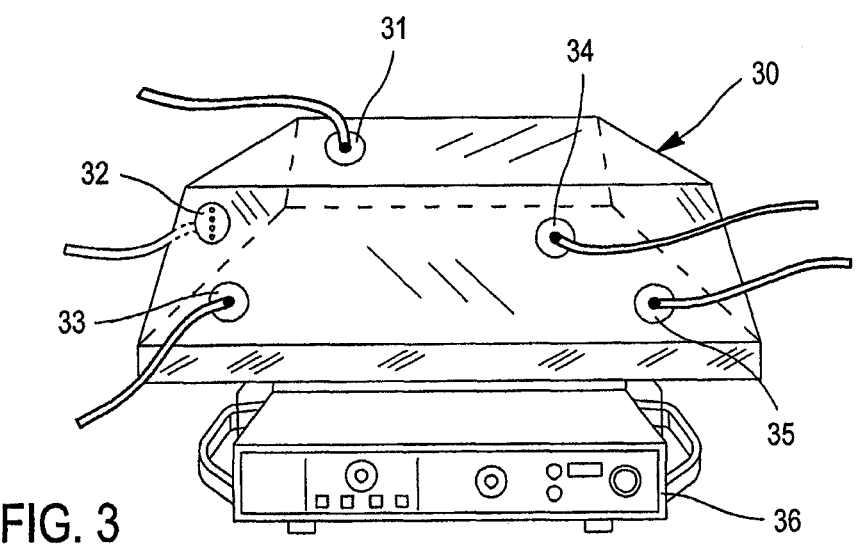
FIG. 3 illustrates a practical example of a single-use bioreactor equipped with single-use sensors according to the invention.

For equipping a single-use bioreactor 20, with reference to FIG. 2, single-use sensors 21, 22, 23 can be installed respectively on one side surface, the base and the front surface of this bioreactor. Thus, as illustrated by FIG. 3, a single-use bioreactor 30 utilized on a control device 36 in continuous use can be supplied fully equipped with single-use sensors 31-35.

Figure 4A:
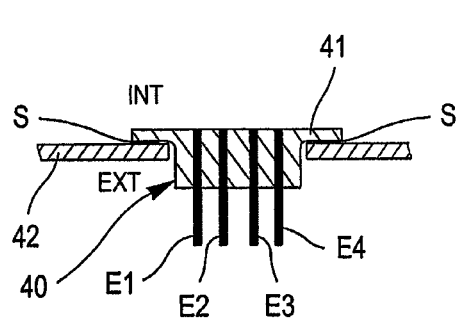
FIG. 4A is a cross-section of a single-use sensor with four electrodes according to the invention.
Figure 4B:
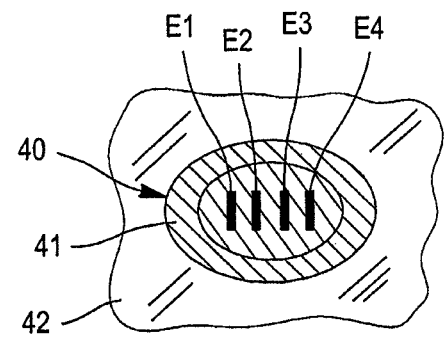
FIG. 4B is a top view of the single-use sensor of FIG. 4A.

With reference to FIGS. 4A and 4B, a single impedance measurement sensor 40 can be arranged in an opening in a wall 42 of a bioreactor, with a detection part a detection surface 41 of which is arranged inside the bioreactor and fixed by welding S to the inner surface of this wall. The impedance measurement sensor then forms an integral part of the bioreactor.

It is also possible to provide other fixing methods such as screwing, shrinking-on or gluing. The sensor 40 is equipped on the detection surface 41 with four electrodes E1-E4, two of which ensure an excitation function and two a measurement function.

Figure 5A:
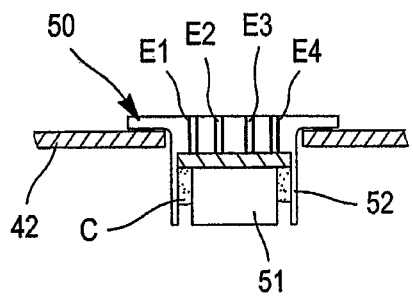
FIG. 5A is a cross-section of a first method of connection of the electrodes of a single-use sensor according to the invention produced from a machined part and utilizing a connector coated with an adhesive.
Figure 5B:
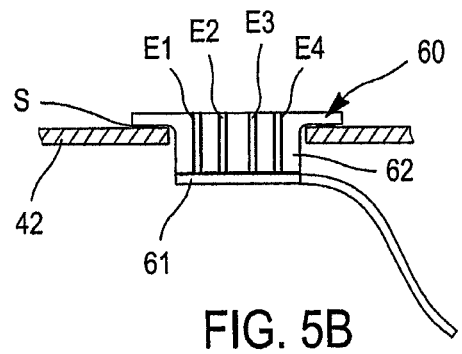
FIG. 5B is a cross-section of a second method of connection of the electrodes of a single-use sensor according to the invention produced from a machined part and utilizing a cable or a flexible component.
Figure 6A:
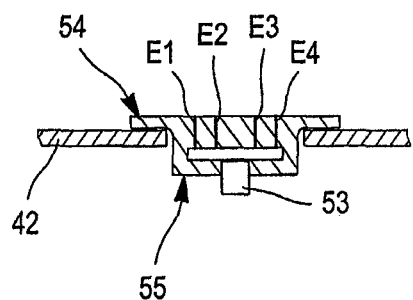
FIG. 6A is a cross-section of a single-use sensor provided with electrodes and with a connector over-moulded by injection.
Figure 6B:
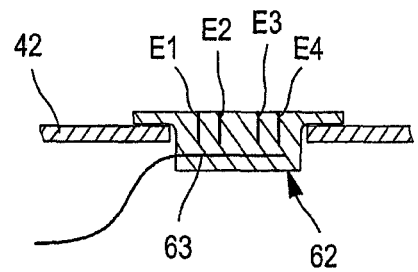
FIG. 6B is a cross-section of a single-use sensor provided with electrodes and with a cable or flexible component over-moulded by injection.

The connection of the electrodes of a single-use sensor to a measurement or control device can be carried out, either by using a connector (FIGS. 5A and 6A), or by using a cable or flexible component (FIGS. 5B and 6B). These connection means constitute the connection part of the single-use sensor.

The single-use sensor can be produced either from a machined plastic part (FIGS. 5A and 5B), or by injection with over-moulding of the electrodes and the connection means (FIGS. 6A and 6B).

The electrodes of a single-use impedance measurement sensor can be produced:
  either in the form of metal parts which can be glued (FIGS. 4A, 4B, 5A, and 5B) or over-moulded (FIGS. 6A and 6B),
  or by deposition, for example by vacuum deposition techniques, by screen-printing, lithography, or electrolysis.

In a first configuration illustrated by FIG. 5A, the single-use sensor 50 inserted into an opening in a bioreactor is produced from a machined part 52 in which four electrodes E1-E4 have been arranged and a connector 51 fixed to the machined part by gluing C.

In a second configuration illustrated by FIG. 5B, the single-use sensor 60, produced from a machined part 62, is equipped with a flexible component or a cable 61 electrically connected to the four electrodes E1-E4.

In a third configuration illustrated by FIG. 6A, the single-use sensor 55 is produced by injection of plastic material with over-moulding of the four electrodes E1-E4 and a connector 53.

In a fourth configuration, the single-use sensor 62 is produced by injection of plastic material with over-moulding of the four electrodes E1-E4 and a flexible component 63.

Figure 7A:
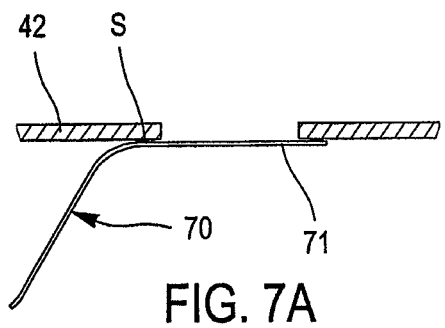
FIGS. 7A, 7B and 7C illustrate a particular example of a single-use sensor according to the invention in which the electrodes are placed directly on a flexible component.
Figure 7B:
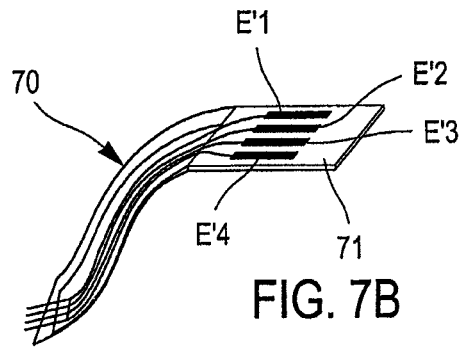
Figure 7C:
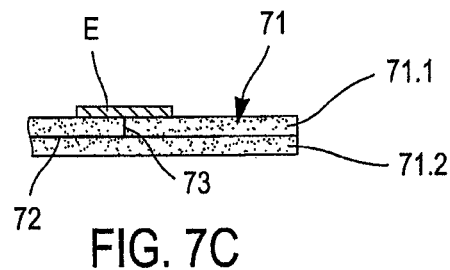

In another embodiment illustrated by FIGS. 7A, 7B and 7C, the electrodes E'1-E'4 of a single-use sensor 70 are produced by deposition of metal directly onto a flexible component 71. This sensor 70 can then be fixed by welding S to the wall 42 of a bioreactor.

With reference to FIG. 7C, the flexible component 71 is produced by superposition of two insulating flexible components 71.1, 71.2 between which a strip conductor 72 is produced, connected to a deposited electrode E by means of a hole 73 passing through the insulating flexible component 71.1 on the outside face of which the electrode E is deposited.

A single-use impedance measurement sensor 40 can be combined with another single-use sensor, for example a fluorescence sensor for measuring the pH, oxygen ($O_2$) or carbon dioxide ($CO_2$).

Figure 8:
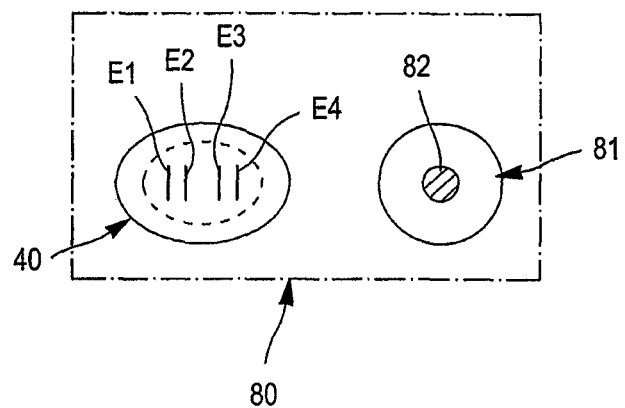
FIG. 8 illustrates a combination of a single-use impedance measurement sensor according to the invention and a single-use fluorescence measurement sensor; in a separate assembly.
Figure 9:
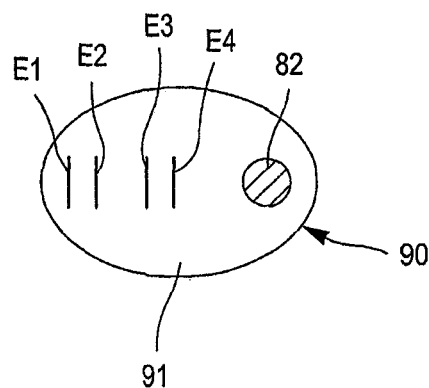
FIG. 9 illustrates the combination of a single-use impedance measurement sensor according to the invention and a single-use fluorescence measurement sensor, mounted on the same support.

The two single-use sensors can be either mounted separately (FIG. 8), or arranged on the same support (FIG. 9). In the first embodiment, each single-use sensor 40, 82 is provided on a separate support 41, 81, whereas in the second embodiment, the active elements of the two sensors —the four electrodes E1-E4 of the impedance measurement sensor, and the fluorescence sensor 82—are arranged on the same patch or support 91 and constitute a single-use double sensor 90.

A description will now be given of the constraints on the production of single-use sensors according to the invention. According to the rules of current good manufacturing practices (cGMP), solvents and all pollutants are to be banned from the manufacturing processes in order to avoid polluting the bio-materials used in the industrial production of the sensor. In particular, the "leachables and extractables" standard (21 CFR part 600.11) must be followed.

The sterilization sequence must not be broken between the manufacture of a sensor and its installation by a sub-contractor. The single-use sensors are sent in sterile packaging and are mounted on the enclosure under a laminar flow. Once all the elements are mounted, the enclosure is sterilized by gamma irradiation.

The materials used must of course be bio-compatible and resistant to the dose of gamma rays utilized.

The single-use sensor must be pre-decontaminated, i.e. be cleansed of any pollutant below a threshold accepted by the application. These pollutants are mainly acquired during the processes used for the manufacture of the sensor (machining, assembly, welding, gluing etc.). The packaging of the single-use sensors is studied in order to preserve the sterility of the sensor and to be compatible with the requirements and constraints for use in a clean room. Therefore, a double-walled packaging is recommended.

The sensor is mounted on the bioreactor and the gamma sterilization is carried out preferably after the mounting of the sensor and of all the constituents (pipes, stoppers, connections etc.). For other applications, the sterilization can be carried out just after the packaging of the sensor. Other means of sterilization can be also envisaged.

The single-use sensors can be connected, by cabled or non-cabled link, to electronic impedance measurement equipment available on the market or to equipment which is more specific to the measurement of biomass such as that disclosed in the document FR2 812 725.

It can also be provided that all or part of the measurement and processing electronics are built-in to in the bioreactor, the packaging or the intelligent container, by using integration technologies, optionally with its' own electricity supply. In particular, optical or sound alarm devices, can also be associated with the single-use sensors according to the invention. For example in the case of intelligent packaging provided for storing a biological medium, an alarm signal can be generated when an abnormal development of the capacitance or of a physical or physico-chemical variable is detected. Reference may in particular be made to the document FR2 874 26 in the name of the present applicant, which discloses a process and device for the determination of biomass in a medium.

Manufacturing techniques resulting from the electronics and microelectronics could be implemented for large-scale manufacture of electrodes of a single-use sensor according to the invention. In particular, an integrated circuit for capacitive detection could be produced by diffusion techniques, for example on polymer substrates or substrates commonly used for producing microsystems.

Of course, the invention is not limited to the examples which have just been described and numerous adjustments can be made to these examples without exceeding the scope of the invention.

The invention claimed is:

1. A single-use bioreactor or container comprising:
   an enclosure provided for containing a biological medium;
   a control device; and
   at least one single-use sensing device for making at least one impedance measurement in a physical, physico-chemical and/or biological process in said biological medium, said sensing device including a detection part with at least four electrodes for impedance measurements on a detection face arranged inside said single-use bioreactor or container so as to be in direct contact with said biological medium, said at least four electrodes being coupled to said control device and designed to avoid effects of double-layer polarization, and said detection part being fixed by gluing or by welding to an inner face of a wall of said enclosure so as to be an integral part thereof;
   wherein said control device is configured to determine parameters of a β dispersion curve from the impedance measurements of said at least four electrodes.

2. The single-use bioreactor or container according to claim 1, wherein the sensing device is associated with at least one single-use physical, physico-chemical or biochemical sensor.

3. The single-use bioreactor or container according to claim 1, wherein the sensing device includes electrodes extending over the detection part.

4. The single-use bioreactor or container according to claim 3, wherein the sensing device is produced in the form of a machined mechanical part arranged for receiving the electrodes on a detection part and a measurement signal output means on a connection part.

5. The single-use bioreactor or container according to claim 4, wherein the sensing device is produced in the form of an injection-molded part including the electrodes on a detection part and the measurement signal output means on a connection part.

6. The single-use bioreactor or container according to claim 4, wherein the measurement signal output means includes a connector.

7. The single-use bioreactor or container according to claim 4, wherein the measurement signal output means includes a cable or a flexible component.

8. The single-use bioreactor or container according to claim 3, wherein said electrodes are produced from metal parts.

9. The single-use bioreactor or container according to claim 4, wherein said electrodes are produced by the deposition of metal on an insulating support.

10. The single-use bioreactor or container according to claim 9, wherein the support for deposition of the electrodes is a flexible component.

11. The single-use bioreactor or container according to claim 10, wherein the flexible support is produced in the form of two insulating films at least one of which supports an electrode produced by the deposition and is electrically connected to a conductor arranged between the two insulating films.

12. The single-use bioreactor or container according to claim 1, wherein the sensing device is arranged in order to be installed in a sterile envelope for multiple applications.

13. The single-use bioreactor or container according to claim 2, wherein the sensing device incorporates an additional single-use physical, physico-chemical or biochemical sensor on a same support.

14. The single-use bioreactor or container according to claim 1, wherein the sensing device also includes built-in means for locally processing impedance measurement signals.

15. The single-use bioreactor or container according to claim 14, wherein the sensing device also includes built-in means for producing an alarm signal in response to the detection of an anomaly by the built-in processing means.

16. A method for producing a single-use bioreactor or container according to claim 1, wherein the sensing device is utilized in a production environment corresponding to the asepsis and sterility criteria required for the use of a bioreactor.

17. The method according to claim 16, wherein the materials utilized for the production of the single-use sensing device are biocompatible and compatible with sterilization by gamma-irradiation.

18. The method according to claim 16, further comprising sterilizing the single-use sensing device after its installation in a bioreactor.

19. The single-use bioreactor or container according to claim 1, wherein two electrodes of the at least four electrodes ensure an excitation function and two other electrodes of the at least four electrodes that differ from the two electrodes that ensure an excitation function, ensure a measurement function.

* * * * *